(12) United States Patent
Schiefermüller et al.

(10) Patent No.: US 8,860,257 B2
(45) Date of Patent: Oct. 14, 2014

(54) METHOD AND APPARATUS FOR THE REMOTE CONTROL OF A POWER SOURCE CONNECTED TO A MANUALLY ACTUATED IMPLEMENT

(75) Inventors: Robert Schiefermüller, Buchkirchen (AT); Wolfgang Brunmayr, Wels (AT); Christian Pointner, Kallham (AT)

(73) Assignee: Fronius International GmbH, Pettenbach (AT)

( * ) Notice: Subject to any disclaimer, the term of this patent is extended or adjusted under 35 U.S.C. 154(b) by 600 days.

(21) Appl. No.: 13/138,556

(22) PCT Filed: Mar. 26, 2010

(86) PCT No.: PCT/AT2010/000090
§ 371 (c)(1),
(2), (4) Date: Sep. 2, 2011

(87) PCT Pub. No.: WO2010/111722
PCT Pub. Date: Oct. 7, 2010

(65) Prior Publication Data
US 2011/0316516 A1  Dec. 29, 2011

(30) Foreign Application Priority Data

Mar. 31, 2009 (AT) ................... A 509/2009

(51) Int. Cl.
| | |
|---|---|
| H01H 1/24 | (2006.01) |
| B23K 9/02 | (2006.01) |
| B23K 9/127 | (2006.01) |
| A61F 9/06 | (2006.01) |
| B23K 9/32 | (2006.01) |
| G06F 3/01 | (2006.01) |
| B23K 9/095 | (2006.01) |
| B23K 9/10 | (2006.01) |

(52) U.S. Cl.
CPC ............ *B23K 9/1087* (2013.01); *B23K 9/02* (2013.01); *B23K 9/1276* (2013.01); *A61F 9/06* (2013.01); *B23K 9/32* (2013.01); *G06F 3/012* (2013.01); *B23K 9/0956* (2013.01); *B23K 9/322* (2013.01)
USPC ........................................................ 307/122

(58) Field of Classification Search
USPC ........................................................ 307/122
See application file for complete search history.

(56) References Cited

U.S. PATENT DOCUMENTS

| | | |
|---|---|---|
| 2,526,597 A | 10/1950 | Winslow |
| 4,266,114 A | 5/1981 | Hansen |

(Continued)

FOREIGN PATENT DOCUMENTS

| | | |
|---|---|---|
| CN | 100376351 C | 7/2005 |
| DE | 10 2006 048 166 | 2/2008 |

(Continued)

OTHER PUBLICATIONS

Japanese Office Action dated May 21, 2013 in Japanese Application No. 2012-502386 with English translation.

(Continued)

*Primary Examiner* — Hal Kaplan
(74) *Attorney, Agent, or Firm* — Collard & Roe, P.C.

(57) ABSTRACT

The invention relates to a method and to an apparatus for operating a power source (1) connected to a manually actuated implement (4) by a user, wherein parameters of the power source (1) are set by way of operating elements (3) of an operating and display unit (2) and a movement of the implement (4) in the space is captured by way of an evaluation unit (9) disposed in the power source (1). In order to enable fast and rapid operation of the power source (1), even without removing a potentially present protective clothing of the user, it is provided for an operating function to be activated at the power source (1), whereupon the movement of the implement (4) in the space (6) is captured and a position of the implement (4) resulting from the movement is associated with the operating and display unit (2).

17 Claims, 4 Drawing Sheets

(56) References Cited

U.S. PATENT DOCUMENTS

| | | |
|---|---|---|
| 4,380,696 A | 4/1983 | Masaki |
| 6,506,050 B1 | 1/2003 | Steddin |
| 6,734,393 B1 | 5/2004 | Friedl et al. |
| 7,291,808 B2 | 11/2007 | Burgstaller et al. |
| 2005/0205541 A1 | 9/2005 | Burgstaller et al. |
| 2007/0070358 A1 | 3/2007 | Ouchi |
| 2008/0082179 A1 | 4/2008 | Yang |
| 2008/0314887 A1 | 12/2008 | Stoger et al. |
| 2009/0237499 A1 | 9/2009 | Kressel et al. |
| 2009/0302015 A1 | 12/2009 | Feitzlmaier et al. |

FOREIGN PATENT DOCUMENTS

| | | |
|---|---|---|
| EP | 2 008 697 A1 | 12/2008 |
| EP | 2 022 592 | 2/2009 |
| JP | H05-149966 A | 6/1993 |
| JP | 5-219580 | 8/1993 |
| JP | 7-44315 | 2/1995 |
| JP | 09-009369 | 1/1997 |
| JP | 10-305366 | 11/1998 |
| JP | 2003-111171 | 4/2003 |
| JP | 2004-160578 | 6/2004 |
| JP | 2005-527381 | 9/2005 |
| JP | 2008-194282 A | 8/2008 |
| JP | 2008-307392 A | 12/2008 |
| WO | WO 03/084706 | 10/2003 |
| WO | WO 03/104965 | 12/2003 |
| WO | WO 2007/009131 | 1/2007 |
| WO | WO 2007/137310 | 12/2007 |

OTHER PUBLICATIONS

International Search Report of PCT/AT2010/000090, Nov. 16, 2010.
Austrian Office Action dated Oct. 29, 2009 in Austrian Application No. A 509/2009 with English translation of relevant parts.
Japanese Office Action dated Jan. 22, 2013 in Japanese Application No. 2012-502386 with English translation.
Chinese Office Action dated Sep. 18, 2013 in Chinese Application No. 201080015159.0 with English translation.

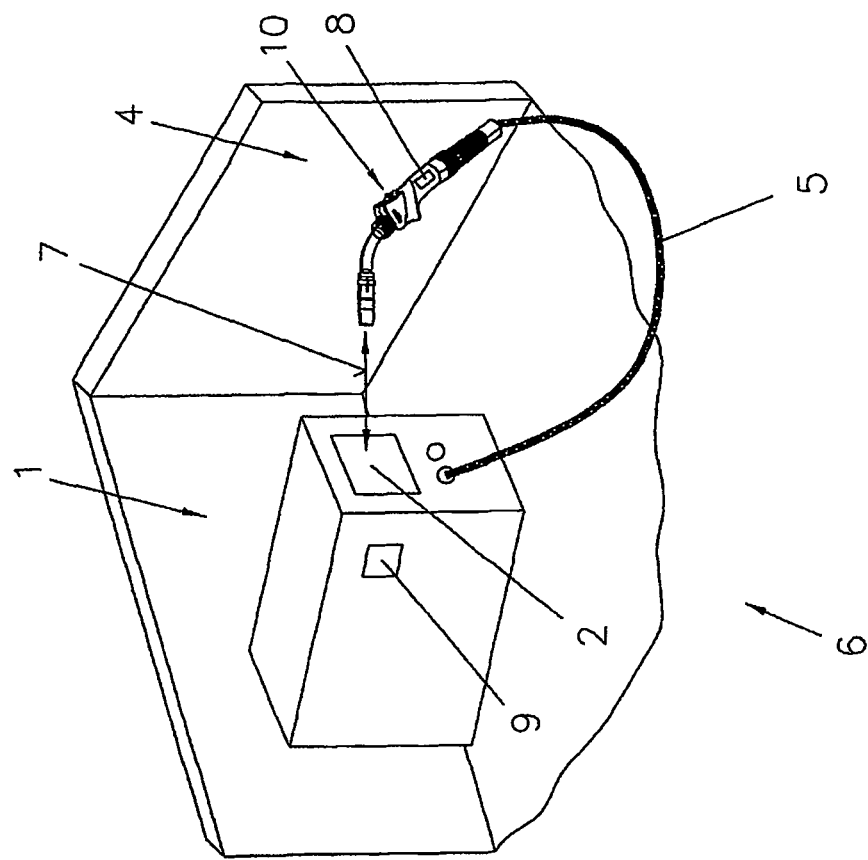
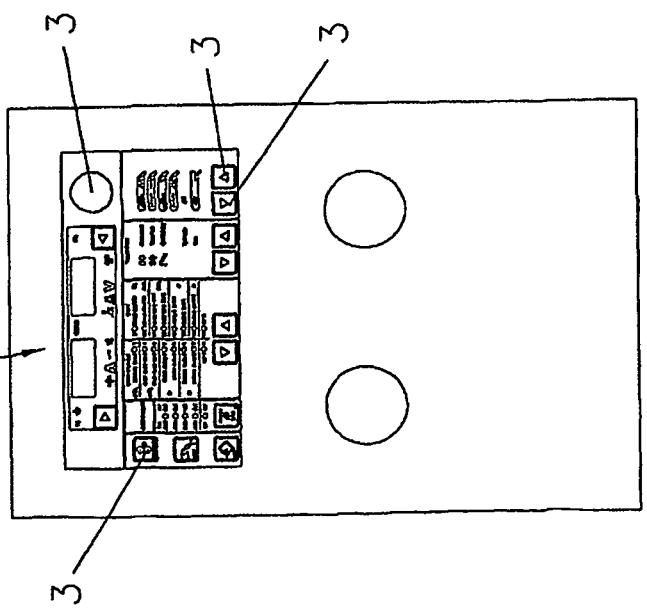

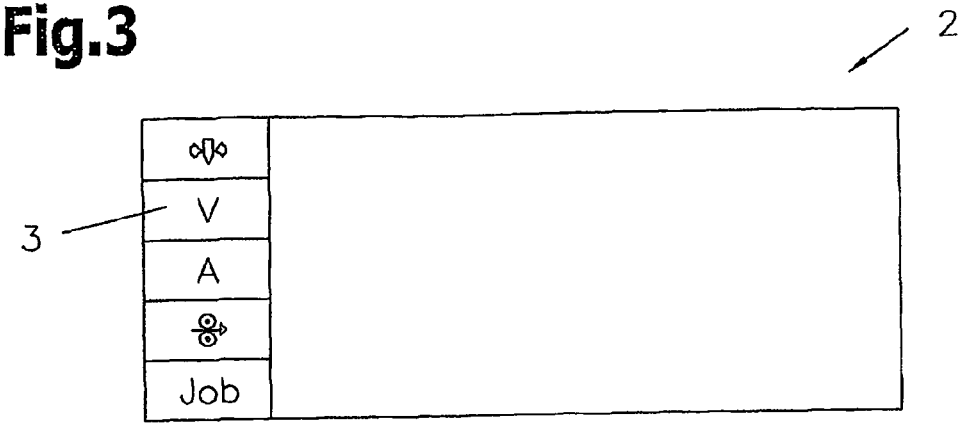
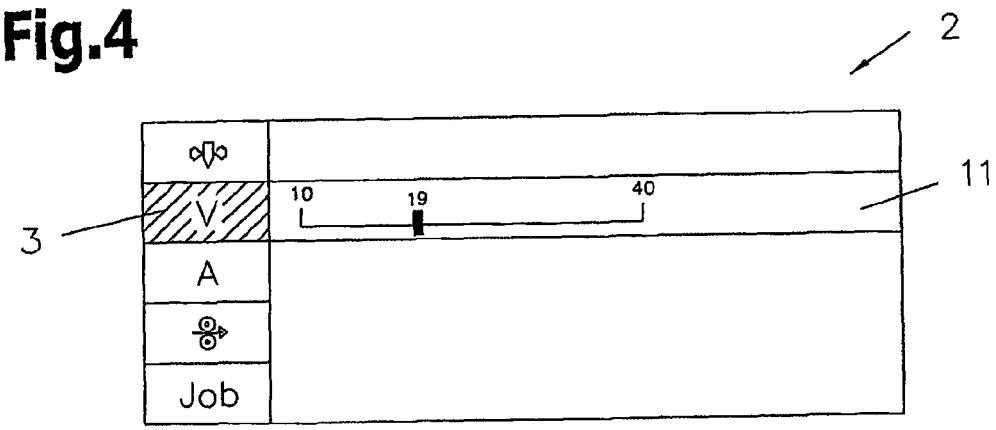
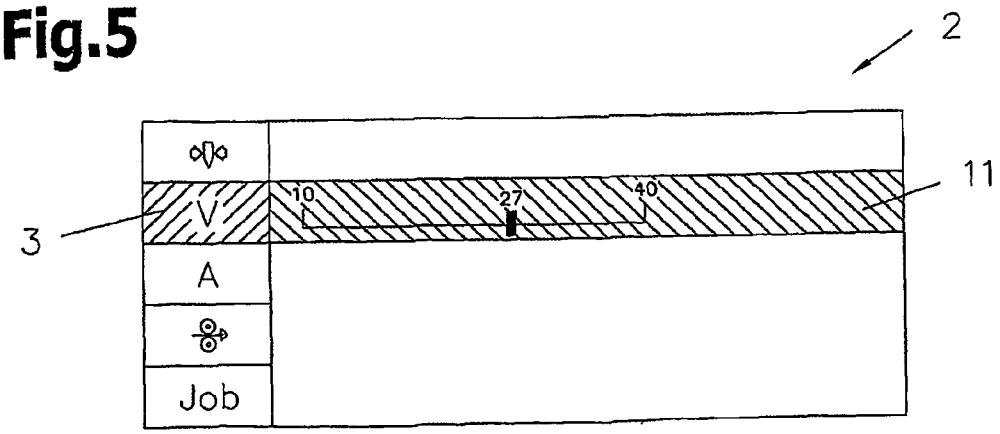

METHOD AND APPARATUS FOR THE REMOTE CONTROL OF A POWER SOURCE CONNECTED TO A MANUALLY ACTUATED IMPLEMENT

CROSS REFERENCE TO RELATED APPLICATIONS

This application is the National Stage of PCT/AT2010/000090 filed on Mar. 26, 2010, which claims priority under 35 U.S.C. §119 of Austrian Application No. A 509/2009 filed on Mar. 31, 2009, the disclosure of which is incorporated by reference. The international application under PCT article 21(2) was not published in English.

The invention relates to a method for operating a power source connected to a manually actuated implement by a user.

The invention further relates to an apparatus, in particular a welding helmet, for operating a power source connected to a manually actuated implement by a user.

The implement is meant to be, in particular but not limited to, a manually actuated welding torch of a welding apparatus. The operating and display unit or the user interface is preferably formed by a touch screen performing both the display and operating functions at the same time.

WO 2007/009131 A1 describes a method and an apparatus for determining the position of the welding torch in three-dimensional space, preferably for quality control. Here it is possible to automatically set and/or modify welding parameters at the power source with respect to the position of the welding torch and/or the position of the welded seam, so faulty settings made by the welder may be avoided.

In general, operating a power source via operating elements, which are controlled by the fingers of a user in a user interface, is known from the prior art.

It is the object of the present invention to provide a rapid and simple operation of a power source without having to remove a potentially present protective clothing such as, in particular, protective gloves.

According to the method, the object of the invention is achieved by activating an operating function at the power source, whereupon the movement of the implement in the space is captured and a position of the implement resulting from said movement is associated with the operating and display unit. This means that the operating function must be activated before operation via movement of the implement can be done. An advantage here is that a very simple operation of the power source may also be done with a potentially present protective equipment and/or protective clothing of the user via the implement in a contact-free manner. There is no need to remove a potentially present protective cover of the operating and display unit on the power source for operation, either. Finally, such a way of operation is independent from the design of the operating and display unit (touch screen, buttons, turning knobs, etc.) as well. Furthermore, the user may determine the position for operation. Thereby, the user does not have to leave a certain working position, for example, in order to operate the power source.

The activation of the operating function at the power source may be done by denoting a reference point corresponding to the position of the implement, by actuating an actuation element on the implement, by positioning the implement at a defined distance from the power source, or by performing a short, sharp movement with the implement.

Advantageously, the movements of the implement in the space are captured by evaluating movements in at least two dimensions of the space or by evaluating the angle of the implement in the space.

For reporting to the user when a position is associated with an operating element, said operating element is preferably denoted and/or marked on the operating and display unit.

Furthermore it may be provided that the associated operating element is confirmed by the user. This confirmation may be given by actuating an actuation element on the implement, by moving the implement, or by touching the operating element on the operating and display unit via the implement.

After confirming the operating element, the at least one parameter of the power source associated with the operating element will be set and/or modified.

According to another feature of the invention the data resulting from the movement of the implement will be evaluated in the power source.

In the course of this, the data can be transferred to the power source via a bus, which is arranged in a hose package between the implement and the power source.

The object according to the invention is also achieved, according to the method, by storing a motion event in the power source, wherein the captured movements of the implement are recorded and compared to the stored motion events in order to identify a motion event, with a functional event being carried out if matches are detected.

The object according to the invention is also achieved, according to the method, by activating a head-up display connected to the power source via an operating function, with at least a part of the operating and display unit being displayed in the head-up display, whereupon the movement of the implement in the space is captured and a position of the implement resulting from the movement is associated with the operating and display unit.

Moreover, the object according to the invention is achieved also by designing the operating and display unit to be electrically conductive and establishing a current flow between the implement and the operating and display unit by touching the implement with the electrically conductive operating and display unit, in particular the operating element.

Finally, the object is also achieved via an aforementioned apparatus, wherein the evaluation unit is designed for implementing the method specified above. An advantage here is that the operating is preferably done exclusively by moving the manually actuated implement without, for example, requiring the actuation of buttons. Further advantages resulting from this can be understood from the above description and the following examples.

In particular, the object according to the invention is also achieved via a welding helmet, wherein the visor of the welding helmet is designed as a head-up display and may be activated via an operating function, and wherein at least a part of the operating and display unit may be displayed in the head-up display, whereupon the movement of the implement in the space may be captured and a position of the implement resulting from the movement may be associated with the operating and display unit.

The present invention will be explained in more detail by means of the attached schematic drawings.

In the drawings:

FIG. 1 shows a schematic representation of a front view of a power source or a welding apparatus;

FIG. 2 shows a schematic representation of a power source or a welding apparatus with a welding torch as an implement in a space;

FIG. 3 to 5 show different views of an operating and display device of a power source;

Figure 6:
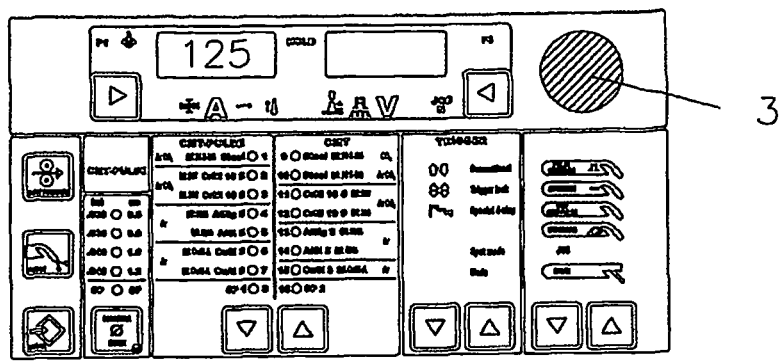
FIG. 6 to 8 show further views of an operating and display device of a power source according to the present invention.

As an introduction, it is noted that like parts of the exemplary embodiment are designated by like reference numerals while all disclosures made in the description can be transferred to correspond to like parts with like reference numerals. Furthermore, single features from the exemplary embodiment(s) shown may also represent independent solutions according to the invention.

A power source 1 is generally operated by a user via a user interface and/or an operating and display unit 2, with the user actuating the operating elements 3 integrated into the operating and display unit 2. For making certain settings concerning the power source 1, in particular before performing a welding process, the operating elements 3 are actuated by the fingers of the user. In most cases, the manually actuated implement 4, in particular the welding torch and possibly a protective glove as well, must be removed before the settings may be entered. Frequently, a plurality of operating elements 3, by which a large number of parameters may be set, is arranged on the operating and display unit 2. Accordingly, most operating elements 3 cannot be actuated when wearing a protective glove. FIG. 1 shows a front view of a power source 1 with an operating and display unit 2 having some operating elements 3 denoted as examples. The operating and display unit 2 is preferably formed by a touch screen which fulfils both the operating and display functions. Below the operating and display unit 2 two connectors, to which the manually actuated implement 4 may be connected via a hose package 5, are illustrated on the power source 1 (see FIG. 2).

According to the invention, operation is done by movements of the implement 4 in a user's hand in the space 6, with a position resulting from the movements being automatically associated with the operating and display unit 2, in particular with an operating element 3, after an operating function has been activated at the power source 1.

Therefore, a parameter of the power source 1 may be set by the user directly via the implement 4, as if the settings were made directly via the operating elements 3 on the operating and display unit 2. For example, a welder is performing the movements with a welding torch or a different manually actuated component of a welding apparatus such as a remote control. The settings via the operating device according to the invention may be made before, after or between work done with the implement 4, i.e. before, after or between welding processes, for example. Operation during welding is not intended. The operating function will be deactivated, for example, by striking an electric arc or applying a high frequency in order to strike an electric arc.

The work flow according to the invention for operating the power source 1 by movements of an implement 4 in a user's hand in the space 6 will be described with reference to FIGS. 2 to 8. The user has the implement 4 in his hand and can operate the operating and display unit 2 of the power source 1 by movements of the implement 4 in an area called operating area. This operating area may be defined in a number of different ways while a reference point is always defined for the implement 4 in the operating area. For example, the implement 4 can be positioned at a defined distance 7 from the operating and display unit 2, thereby defining a reference point and automatically switching to the operating function of the power source 1 and/or activating it. Thereby, the user can view the operating and display unit 2 and make the settings in a controlled manner. On the other hand, switching to the operating function may also be carried out via an actuation element 10 on the implement 4, said actuating of the actuation element 10 defining a reference point at the same time. For this, a separate actuation element 10 may be arranged on the implement 4 or present actuation elements 10—such as those for carrying out welding processes—may be used. Present actuation elements 10 must, for example, be actuated for a defined time span, with the position of the element 4 preferably being independent from the distance or direction with respect to the operating and display unit 2.

Switching to the operating function may, however, also be achieved by directing the implement 4 towards the power source 1. In this case, the reference point is defined as soon as "visual contact" between the implement 4 and the operating and display unit 2 and/or the power source 1 is established. Switching is also possible by a short, sharp movement of the implement 4, such as a knock.

This switching thus effects that the implement 4 changes, for example, from a welding mode to an operating mode. By changing to the operating mode, the operating function is activated while preferably certain functions of the power source 1 are deactivated for safety reasons. For example, the power element of the power source 1 may be turned off so that no welding current can be supplied in case of accidentally incorrect operation. To give another example, a gas supply may also be interrupted.

After switching to the operating function, a reference point, from which the user can operate the operating and display unit 2 by movements of the implement 4, will be defined—for example in the centre—displayed on the operating and display unit 2. This means that the movements are performed with respect to the reference point, with the reference point in the operating and display unit 2 substantially corresponding to the reference point in the operating area. For example, an operating element 3 may be denoted and/or marked as a reference point, such as by a change in colour or by a light-emitting diode. Thereby the user knows his position on the operating and display unit 2 and can mark the desired operating element 3 by moving the implement 4 accordingly. For this purpose, a unit 8 is integrated into the implement 4, said unit 8 generating a signal depending on the position of the implement 4 and sending it to the power source 1, where said signal is evaluated by an evaluation unit 9. The operating element 3 associated with the current position of the implement 4 will be denoted and/or marked on the operating and display unit 2. The implement 4 will substantially move a cursor on the operating and display unit 2 and/or navigate through it. The operating and display unit 2 may be formed by a graphics display, a membrane keyboard, a touch screen or the like.

The movements of the implement 4 are preferably captured by the coordinates (x, y, z) of the three-dimensional space 6 and/or by changes of the angle. In this case, the angle refers substantially to the movements of the wrist, with the coordinates and/or position of the hand remaining substantially unchanged. As a consequence, the position and/or the coordinates of the implement 4 are changed by altering the angle (up/down or left/right), thereby moving, for example, a cursor on the operating and display unit 2. Here the cursor can be moved continuously on the operating and display unit 2, or the cursor may be associated with the closest operating element 3 of the operating and display unit 2, according to the movement. Once the desired operating element 3 has been marked, i.e. once the position of the implement 4 has been associated with the desired operating element 3, the user can confirm the association, preferably by actuating the actuation element 10. Depending on the field of application of the power source 1, the confirmation, for example via a button, may trigger different procedures:

One procedure may be that the parameter of the power source 1 is modified immediately when an operating element 3 is actuated. Here the operating element 3 corresponds directly to the respective parameter, as is the case when selecting the welding method.

Another procedure may be that the operating element 3 corresponds directly to a parameter of the power source 1, but in addition, a value for the parameter has to be set, so after confirming the operating element 3 on the operating and display unit 2, the value may be set.

Similarly, the procedure triggered may be such that after confirmation of the associated operating element 3, a parameter has to be selected, and then its value has to be set by moving the implement 4. This applies also if the associated parameter is a menu item.

Figure 7:
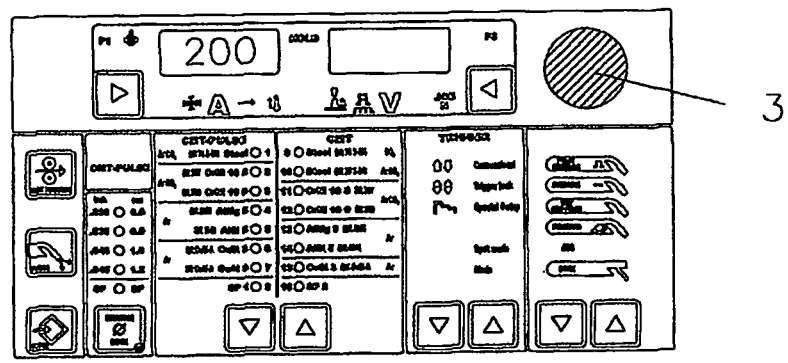

Setting the value of a parameter may be done in different ways, so the setting options described below are to be regarded as examples only:

The value may, for example, be set by a bar 11 being displayed on the operating and display unit 2, on which the current value is marked and may be changed by moving the implement 4 (see FIGS. 3 to 5). For example, an operating element 3 is selected on the operating and display unit 2. As the association of the position of the implement 4 is confirmed according to the marked operating element 3 by the actuation button 10, a bar 11 with the current value will appear next to it. If the bar 11 is now marked and confirmed by moving the implement 4, the value may be changed and confirmed by further movements. Afterwards, the view of the operating and display unit 2 will return to its initial configuration according to FIG. 3. In the same way a turning knob may also be denoted and/or marked as an operating element 3 on the operating and display unit 2, so that the implement 4 has to be moved in a corresponding circular manner in order to change the associated value, as is schematically illustrated in FIGS. 6 and 7. After confirming the marked operating element 3 and/or the turning knob, the value may be changed via a circular movement of the implement 4, for example from "125" to "200", and confirmed.

Figure 8:
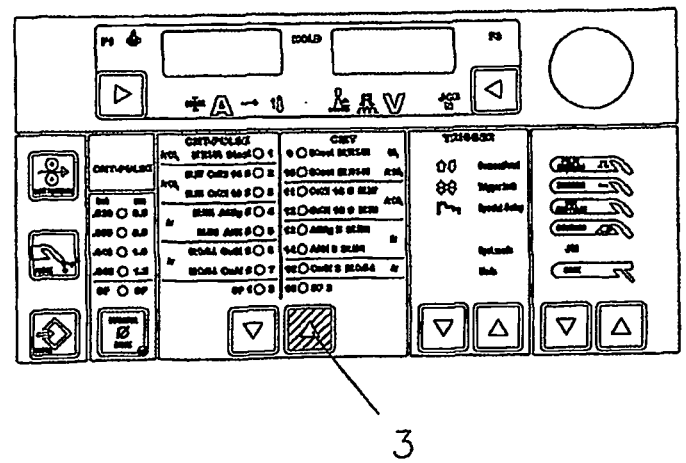

According to FIG. 8, a procedure may, however, also be the selecting and denoting, for example with a light-emitting diode, of a desired parameter by confirming a marked operating element 3 several times. For setting the value of the parameter, corresponding elements to increase and/or decrease the value may be displayed instead of a bar 11. This may be done, for example, in such a way that the value is changed accordingly by marking an element. The change may also be effected by actuating the button. Additionally, the value to be set may be displayed on a display on the implement 4. For these setting options, evaluating two dimensions of the movement of the implement 4 is sufficient. Evaluating three dimensions of the movement of the implement 4 may be required, for example, if the working point for the welding method is dislocated on a characteristic line and said characteristic line is displayed in a three-dimensional way on the operating and display unit 2.

Having said this, the user can make all settings on the power source 1 by movements of the implement 4 in his hand and, possibly, an actuation element 10 on the implement 4.

When using a graphics display, for example, this may be done by operating a pointer element in the form of a symbolic welding torch or an arrow via the implement 4, i.e. when moving the implement 4 in the space 6, the position and movement will be captured and transferred to the pointer element. If the implement 4 is moved upwards, for example, the pointer element on the operating and display unit 2 will also move upwards. In the same way the pointer element may be dislocated and/or moved to the left, to the right, downwards, circularly or in any way by moving the implement 4 accordingly in the air. In order to make such control by moving the implement 4 in the space 6 easier for the user, as operating elements 3 close to each other are often harder to select over a distance, a special operating and display unit 2 of the power source 1 may be used. Here the user may, for example, set that he wishes to perform control via an implement 4 on the power source 1 of a welding apparatus, whereupon the operating and display unit 2 will be changed. For example, the conventional operating method will use a representation of an operating and display unit 2 that is different from the one used when making settings via the implement 4. Preferably, when making settings via the implement 4, the operating and display unit 2 is designed more simple and the selectable operating elements 3 therein are displayed larger. Thereby, moving the pointer element to the corresponding operating elements 3 is made easier for the user. For this, the operating and display unit 2 comprises several levels in order to provide all setting options to the welder. On the first level, for example, only the most basic operating elements 3 for the welding current, the speed of the wire feed etc. as well as a further operating element 3 for switching to further settings are displayed. If the user selects an operating element 3 via the pointer element and activates it, a new operating and display unit 2 will open, in which the user can perform the setting of the selected parameter by a bar 11, the entering of values, a simulated rotating wheel etc. In this way the operating elements 3 may also be accessed safely from a larger distance. Of course the welder can also adjust the size of the icons of the operating elements 3 in accordance with his personal requirements. As a consequence, it is possible to display more parameters on one level again. Preferably, the welder can customise the operating and display unit 2 for operation according to his requirements and proficiency.

It should be noted that the movements for the operation are not comparable to the movements during a welding process, so it might be feasible to effect a switch to the operating function by exploiting this difference alone. After the settings have been made, the operating function will be finished, so that the user can use the implement 4 in the conventional way, for example for performing a welding process. Finishing the function and/or switching to the working mode is done by actuating the actuation element 10 or removing the implement 4 from the operating and display unit 2, for example, as opposed to switching to the operating function. As a consequence, the implement 4 can be used to activate or deactivate the operating and/or perform a log-on or log-off to/from the operating.

There are multiple ways for designing and adjusting the unit 8 in the implement 4 and the evaluation unit 9 in the power source 1. Some examples are given below:

The unit 8 may be formed by an infrared camera and the evaluation unit may be formed by two reference points in the operating and display unit 2. This way, the position of the implement 4—substantially the coordinates in the two-dimensional and/or three-dimensional space—may be determined with respect to the power source 1. Accordingly, the position of the movement of the implement 4 may be associated with an operating element 3. The data are preferably transferred via a bus in the hose package 5.

The unit 8 may also be formed by an infrared LED and the evaluation unit 9 may be formed by an infrared camera. Again the position and/or position changes due to movements of the implement 4 can be detected and associated with an operating element 3 on the operating and display unit 2.

The unit 8 in the implement 4 may, however, also be formed by at least one sensor, such as a tilt sensor, an acceleration sensor or a gyro sensor, the data of which are evaluated by a corresponding software of the evaluation unit 9. The position of the movement may thus be associated with an operating element 3 on the operating and display unit 2 accordingly.

The unit 8 and the evaluation unit 9 may also perform generally separate functions. For example, the distance between the implement 4 and the operating and display unit 2 may be detected by respective sensors, and individual sensors may be used to detect the position of the implement 4. It is also possible for the unit 8 to evaluate movements of the implement 4 and perform corresponding steps. Supply of the unit 8 and the sensors, if applicable, may be provided by the hose package 5. Preferably, the data transfer via a serial data bus happens within the hose package 5 as well, or wireless as an alternative.

According to the invention it is also provided that by at least one motion event of the implement 4 in the space 6 an action and/or a functional event is triggered. This can be achieved, for example, under the same conditions as for the operation of the operating and display unit 2 as described above. That is, firstly, before, after or between welding processes or the like. Second, at a defined distance 7 from the power source 1 and, third, by actuating the actuation element 10. In this way it is guaranteed that no operating actions are being triggered during a welding process. An action may be triggered by an abrupt position change of the implement 4, which is initiated by corresponding movements. The abrupt changes may result from vibrations within the implement 4, such as knocking, or by at least one certain motion event. The action can thus be effected, for example, by a sharp lateral or vertical movement, by passing over an acceleration limit or by a time-dependent position change. Such events are accordingly configured into an action by the user, or events are already stored in a memory. Therefore, the motion event performed by the user can be compared to the stored events while the performed motion events are recorded accordingly. As a consequence, no reference point is required, as the operating is carried out by means of the motion event. For example, the lighting of the implement 4 may be turned on, or a predefined welding setting, called a welding job, may be modified. The power source 1 can also switch to "standby mode" if the implement 4 is not being moved for a defined time span, or switch to normal operation mode if the implement 4 is being moved after a defined time span. At the same time, a process called pre-purging with gas, which is required for welding processes, could be started as well. Another possibility is that in case of abrupt position changes of the implement 4, acceleration values are captured to effect certain actions depending on them. Comparing a position change of the implement 4 and the position of the power source 1, for example, could trigger the action of the power source 1 being turned off because the implement 4 has been dropped. As a consequence, there will be no operation on the operating and display unit 2 via the implement 4, but operation of the power source 1 in a conventional manner will be performed.

Such actions may also be identified in welding mode and/or operation mode. In the same way, said actions may be combined. For example in such a way that the lighting—such as a light-emitting diode (LED)—of the implement 4 is switched on and switched off accordingly when the implement 4 is no longer moved. Here, "standby mode" may be activated in addition. Further actions may include threading the welding wire, performing a gas test and/or the like.

Of course the unit 8 and, if applicable, further sensors of the implement 4 might also be arranged within a protective glove used for holding the implement 4. Thereby, a better shielding may be achieved and accuracy may be increased. Supply can again be provided via the hose package 5, wherein the protective glove must be connected to the implement 4.

In general, it should be added that the operating and display unit 2 may also be arranged remotely from the power source 1, such as on a wire feed or an external monitor. Furthermore, it is also possible for operating and display units 2 to be arranged on both the power source 1 and the wire feed device. In this case, an evaluation unit 9 is associated with each operating and display unit 2, with operation—especially for different operating and display units 2 on power source 1 and wire feed device—being possible on only one operating and display unit 2. This decision can be made, for example, in such a way that the operating and display unit 2 of the very device to which the implement 4 is connected will be operated. It is also possible to operate the operating and display device 2 that is closer to the implement 4. The actuation unit 9 associated with the operating and display unit 2 that is not operated will be deactivated. An evaluation unit 9 may also be deactivated manually by the user. Moreover, the operating and display unit 2 may be formed by a head-up display in the visor of a user's helmet. With this, operation of the power source 1 can be done directly from the operator's position as the operating and display unit 2 is displayed in the head-up display. The function of the operation, as it has been described, remains substantially unchanged. Operation can, however, also be carried out via a 3D screen representing the operating and display unit 2 accordingly.

Figure 9:
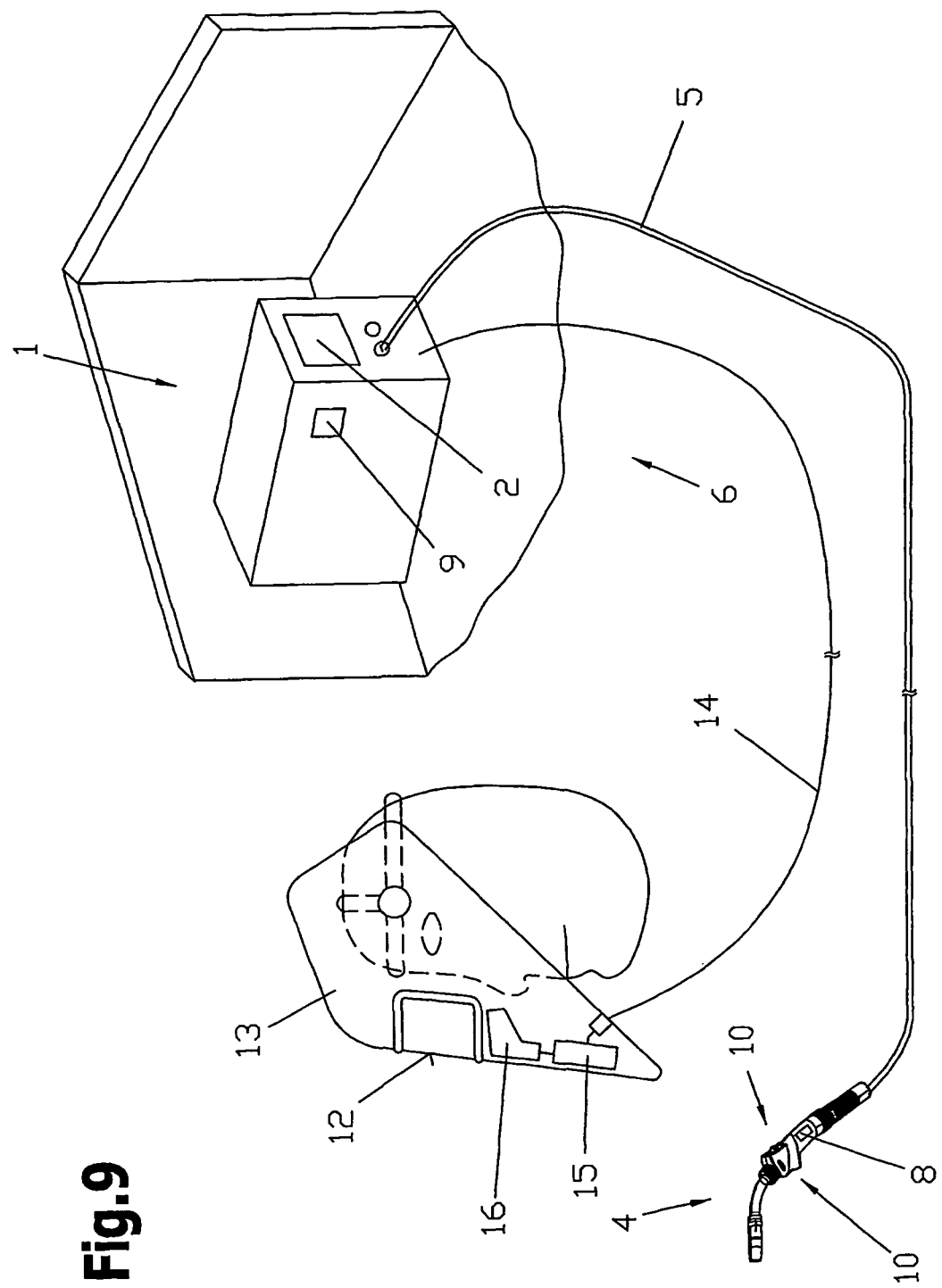
FIG. 9 shows a view of a welding helmet for carrying out the operating method according to the present invention.

FIG. 9 shows the use of a head-up display 12 in a welding helmet 13, welding screen, hand welding screen or welding shield for performing the method according to the invention. For better understanding, parts of what has already been mentioned will be repeated and referred to. After finishing a welding process or before a welding process, the welder or user will actuate a respective combination of keys, in particular the actuation element 10 on the torch or implement 4, to activate the head-up display 12 in the visor of the welding helmet 13 and display the operating function. Preferably, it is not possible to activate the head-up display 12 by accidentally pressing the corresponding actuation element 10 during a welding process. To avoid this, a corresponding safety mechanism may be installed, wherein the control device of the power source 1 will check whether an electric arc has been struck or not if the actuation element 10 is actuated before the head-up display 12 has been activated. If an electric arc is present, turning on the head-up display 12 will be prevented so the visor can continue to protect the user against the electric arc and vision is not impaired by the welding helmet 13, and no undesired modification of the welding parameters can happen due to movement of the torch during the welding process.

As has already been described above, the operating function is preferably activated by the actuation element 10 on the implement 4, whereby the power source 1 will switch to operating mode, the head-up display 12 will be activated by the power source 1, and at least a part of the operating and display unit 2 will be displayed in the head-up display 12. The power source 1 detects the presence of the head-up display 12 via a connected data connection and/or a supply connection. These connections may be designed wireless and/or line-based—for example via a data bus installed within the hose package 5 or a connection line 14. Of course, a direct connection between the implement 4 and the head-up display 12 is possible as well. For displaying the operating function in the head-up display 12 a corresponding imaging device 15 and possibly an evaluation device 16 are arranged within the welding helmet 13 and/or the power source 1. A switch integrated into the welding helmet 13, for example, is connected to the evaluation device 16, said switch being designed to also activate the head-up display 12 and/or the operating function.

The welder has also the opportunity to use the operating and display unit 2 on the welding apparatus and/or the power source 1 in order to set preferences for the design of the operating function displayed in the head-up display 12. Here the welder can decide whether the interface for the head-up display 12 will look the same as the design and/or display on the welding apparatus 1, or whether a modified representation will appear. For example, a simplified interface with fewer setting items may be used, opening a sub-window when an item is selected. This is advantageous because the icons or operating elements 3 can be displayed larger in the head-up display 12, making operation for the welder easier. The welder can compose corresponding masks with appropriately selected welding parameters to be displayed in the head-up display 12, in particular as a main mask, so he can fix the settings for his welding process as quick as possible and does not have to load different masks. Thereby, a full customisation of the interface of the operating function for the head-up display 12 is possible.

In the same way, the reference point will be shown in the head-up display 12 when activating the operating function, so that navigation is possible and/or the operating element 3 will be denoted and/or highlighted in colour, with movements of the torch moving the colour markers to other operating elements 3. In this way, movements of the implement 4 make it possible to associate operating elements 3 in the head-up display 12 according to their positions and set corresponding parameters. The implement 4 is substantially moved above the workpiece or at the operator's position, i.e. independent from the position of the power source 1, so that the reference point in the head-up display 12 is moved with respect to the movements of the implement 4. Accordingly, the reference point is—as has already been described—associated with the desired operating element 3 and, if applicable, confirmed, so that the settings can be made. This has the big advantage that now the user does not have to turn away from the workpiece, but can move the reference point in the head-up display 12 by moving the welding torch directly above the workpiece in the air and/or space, thereby being able to access and modify a respective setting by selecting an operating element 3 with the reference point, preferably when activating a sensor. If the user does not wish to make a setting via the head-up display 12 and/or the head-up display 12 has not been activated, he has to stand up and turn towards the welding apparatus, in particular towards the operating and display unit 2, after finishing the welding process in order to see the reference point on the operating and display unit 2 and dislocate or move it to a respective operating element 3 by moving the torch in the air accordingly. The setting process will thus take much longer and the welder has to change his position with respect to the workpiece as well, which is not necessary when employing a head-up display 12.

As has already been mentioned, it is, of course, generally possible to make the settings, such as increasing or decreasing a value for the welding current, the welding voltage, the speed of the wire feed or the like, via further standard switches or standard buttons arranged on the implement 4, such as the at least one actuation element 10 that is arranged on the top face of the implement 4. That is to say, the user will carry out the operating via the head-up display 12 in exactly the same way as via the operating and display unit 2 on the power source 1. Deactivating the head-up display 12 is done in substantially the same way as deactivating the operating function of the operating and display unit 2 on the power source 1. In order to do this, the actuation element 10 will be actuated for a defined time span, for example, or an operating element 3 for ending the operating function will be selected by the implement 4. After deactivating the head-up display 12, the welding helmet 13 will return to its standard function, so the user is protected against electric arcs in welding processes. Of course, currently set values such as the welding current or the speed of the wire feed can be displayed via the head-up display 12 during the welding process nevertheless, so the user can keep track of the currently active values of certain welding parameters. Preferably, the user can again select a certain choice of welding parameters to be displayed during a welding process. Here it is of substantial importance to make this display preferably transparent and place it in selected areas of the viewing window in order to limit the user's view only marginally.

To sum it all up, it can be said that the head-up display 12 integrated into the welding helmet 13 or welding screen enables the user to fully operate the welding apparatus with the complete welding equipment and without having to be at the welding apparatus or having to turn to it. By actuating an actuation element 10, a head-up display 12 will be activated in the welding helmet 13, with an operating element 3 being marked, for example, as a reference point and/or with a colour marker for the current position of the implement 4. By movements of the implement 4 the reference point or the colour marker will be moved to the very operating element 3 where the settings are to be made. The safety mode provides that operation via the torch is not possible and/or deactivated during welding processes. Of course the invention may be used in the same manner for a cutting process. In general, the head-up display 12 may also be substituted by equivalent display elements such as a transparent screen.

Of course the power source 1 may also be operated directly via the operating elements 3 on the operating and display unit 2 in addition. This type of operation may, for example, be used for the basic configuration while the operation according to the invention via the implement 4 is used for fine tuning after performing welding tests.

The operation according to the invention may also be carried out by minimising the distance 7 between the implement 4 and the operating and display unit 2. Here the operating elements 3 are substantially actuated directly by the implement 4, and settings are made. This type of operation may also include an electric arc of extremely low energy between the operating and display unit 2 and the implement 4 and/or activating a current flow between the implement 4 and the operating and display unit 2 via the actuation element 10 to mark and/or select the desired operating element 3. When the implement 4 is contacted with the operating and display unit 2 afterwards, the electric arc is quenched because of a short circuit and the operating element 3 is actuated.

The invention claimed is:

1. A method for operating a power source connected to a manually actuated implement by a user, wherein the power source is switchable between an operating function and a standard function, wherein during the operating function parameters of the power source are set by way of operating elements of an operating and display unit on the power source and a movement of the implement in a space is captured by an evaluation unit arranged in the power source, wherein the operating function of the power source is activated before, after or between work done with the implement, whereupon the movement of the implement in the space is captured and an association is created between a position of the implement resulting from said movement and an operating element of the operating and display unit for setting and/or modifying at least one parameter of the parameters of the power source, and the association between the position and the operating element is confirmed, the at least one parameter of the parameters of the power source associated with the operating element is set and/or modified after confirming the association between the position and the operating element, and then the operating function of the power source is deactivated again.

2. The method according to claim 1, wherein the operating function of the power source is activated when a reference point corresponding to the position of the implement is denoted on the operating and display unit (2).

3. The method according to claim 1, wherein the operating function of the power source is activated when an actuation element on the implement is actuated.

4. The method according to claim 1, wherein the operating function of the power source is activated when the implement is positioned at a defined distance from the power source.

5. The method according to claim 1, wherein the operating function of the power source is activated by performing a short, sharp movement with the implement.

6. The method according to claim 1, wherein the movements of the implement in the space are captured by said movements being evaluated in at least two dimensions of the space.

7. The method according to claim 1, wherein the movements of the implement in the space are captured by the angle of the implement in the space being evaluated.

8. The method according to claim 1, wherein when associating the position with the operating element, said operating element is denoted on the operating and display unit.

9. The method according to claim 1, wherein the association between the position and the operating element is confirmed by an actuation element on the implement being actuated.

10. The method according to claim 1, wherein the association between the position and the operating element is confirmed by the movement of the implement.

11. The method according to claim 1, wherein the association between the position and the operating element is confirmed by said operating element being touched by the implement on the operating and display unit.

12. The method according to claim 1, wherein the data resulting from the movement of the implement are evaluated in the power source.

13. The method according to claim 12, wherein the data are transferred to the power source via a bus arranged in a cable-hose assembly between the implement and the power source.

14. A method for operating a power source connected to a manually actuated implement by a user, wherein the power source is switchable between an operating function and a standard function, wherein during the operating function parameters of the power source are set by way of operating elements of an operating and display unit on the power source and a movement of the implement in a space is captured by an evaluation unit arranged in the power source, wherein the operating function of the power source is activated before, after or between work done with the implement, whereupon the movement of the implement in the space is captured and the captured movements of the implement are recorded and compared to motion events stored in the power source in order to identify a motion event, with a functional event associated with the stored motion event being carried out if matches are detected, and then the operating function at the power source is deactivated again.

15. A method for operating a power source connected to a manually actuated implement by a user, wherein the power source is switchable between an operating function and a standard function, wherein during the operating function parameters of the power source are set by way of operating elements of an operating and display unit and a movement of the implement in a space is captured by an evaluation unit arranged in the power source, wherein a head-up display connected to the power source is activated by way of the operating function which is activated before, after or between work done with the implement, and at least a part of the operating and display unit is displayed in the head-up display, whereupon the movement of the implement in the space is captured and an association is created between a position of the implement resulting from said movement and an operating element of the operating and display unit for setting and/or modifying at least one parameter of the parameters of the power source, and the association between the position and the operating element is confirmed, the at least one parameter of the parameters of the power source associated with the operating element is set and/or modified after confirming the association between the position and the operating element, and then the operating function of the power source is deactivated again.

16. An apparatus for operating a power source connected to a manually actuated implement by a user, wherein an operating and display unit with operating elements is arranged on the power source, and an evaluation unit is arranged in the power source (1) in the region of the operating and display unit, wherein the evaluation unit is designed for implementing the method according to claim 1.

17. A welding helmet for a user of a power source with a manually actuated implement, wherein the power source is switchable between an operating function and a standard function, wherein during the operating function parameters of the power source may be set by way of operating elements of an operating and display unit on the power source, and a movement of the implement in a space may be captured by an evaluation unit arranged in the power source, with a visor integrated into the welding helmet, with an apparatus for operating the power source according to claim 16, wherein the visor is designed as a head-up display and may be activated by way of the operating function before, after or between work done with the implement, and at least a part of the operating and display unit may be displayed in the head-up display, whereupon the movement of the implement in the space may be captured and an association is created between a position of the implement resulting from said movement and an operating element of the operating and display unit for setting and/or modifying at least one parameter of the parameters of the power source, and the association between the position and the operating element may be confirmed, the at least one parameter of the parameters of the power source associated with the operating element may be set and/or modified after confirming the association between the position and the operating element, and then the operating function may be deactivated again.

* * * * *